United States Patent [19]

Urban

[11] 4,038,392
[45] July 26, 1977

[54] 3-(HETEROCYCLICTHIOMETHYL) QUINOXALINE-1,4-DIOXIDES

[75] Inventor: Frank J. Urban, Niantic, Conn.

[73] Assignee: Pfizer Inc., New York, N.Y.

[21] Appl. No.: 622,057

[22] Filed: Oct. 14, 1975

[51] Int. Cl.² .................. C07D 403/12; A61K 31/495
[52] U.S. Cl. ..................................... 424/250; 424/251; 260/250 QN; 260/256.5 R; 426/532
[58] Field of Search .................... 424/250; 260/250 Q, 260/250 QN, 256.52

[56] References Cited

U.S. PATENT DOCUMENTS

| | | | |
|---|---|---|---|
| 3,558,624 | 1/1971 | Ley et al. | 260/250 QN |
| 3,803,145 | 4/1974 | Abushanab | 260/250 QN |
| 3,845,047 | 10/1974 | Egli | 424/250 |
| 3,931,174 | 1/1976 | McFarland | 260/250 QN |

Primary Examiner—Donald G. Daus
Assistant Examiner—Mark L. Berch
Attorney, Agent, or Firm—Connolly and Hutz

[57] ABSTRACT

2-Substituted-3-thiomethylheterocyclic-quinoxaline-1,4-dioxides are prepared from 2-substituted-3-bromomethyl-quinoxaline-1,4-dioxides and heterocyclic thiols. Oxidations yield the corresponding sulfoxides and sulfones. These compounds are effective in treating bacterial diseases in poultry, swine and cattle.

4 Claims, No Drawings

3-(HETEROCYCLICTHIOMETHYL) QUINOXALINE-1,4-DIOXIDES

BACKGROUND OF THE INVENTION

Continuing synthetic efforts to discover new and more useful antibacterial agents have led, over the years, to the development of a variety of prototype organic compounds including numerous analogs of quinoxaline-1,4-dioxides: J. Chem. Soc., 2052 (1956); Helv. Chim. Acta., 29, 95 (1946); Tetrahedron Letters, 3253 (1965); J. Org. Chem., 31, 4067 (1966); Agnew. Chem. Internat. Edit., 8, 596 (1969); U.S. Pat. Nos. 3,679,679; 3,728,345; 3,753,987; 3,763,162; 3,767,657; 3,803,145; 3,818,007; 3,433,871; 3,371,090; and Belgian Pat. No. 721,728.

A number of these compounds are active against bacteria and protozoa and act as growth promotants in swine and poultry.

SUMMARY OF THE INVENTION

This invention is concerned with quinoxaline- 1,4-dioxides with antibacterial properties having the formula and the pharmaceutically-acceptable acid addition salts such as the hydrochloride, hydrobromide, sulfate, phosphate, nitrate, acetate, propionate, citrate, malate, tartrate, benzoate, succinate, maleate and fumarate;

wherein $R_1$ is hydrogen, lower alkyl ($C_1$-$C_6$), α-hydroxylower alkyl, lower alkanoyl,

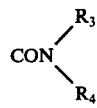

where $R_3$ and $R_4$ are selected from the group consisting of hydrogen, lower alkyl, lower hydroxylalkyl and lower aminoalkyl; and $R_2$ is $CH_2S(O)_m$—$(CH_2)_n$- heterocycle where $m = 0–2$, $n = 0–6$ and heterocycle is selected from the group consisting of 2-imidazolyl, 1-lower alkyl-2-imidazolyl, 2-benzimidazolyl, 1-lower alkyl-2-benzimidazolyl, 2-benthiazolyl, pyridyl and 2-pyrimidinyl.

DETAILED DESCRIPTION OF THE INVENTION

The quinoxaline-1,4-dioxides of the present invention may be prepared by one or more of the following exemplified synthetic routes from starting materials prepared by methods described in U.S. Pat. No. 3,371,090:

A. Amide Route
 1. Displacement
 2. Oxidation of sulfide to sulfone
 3. Oxidation of sulfide to sulfoxide

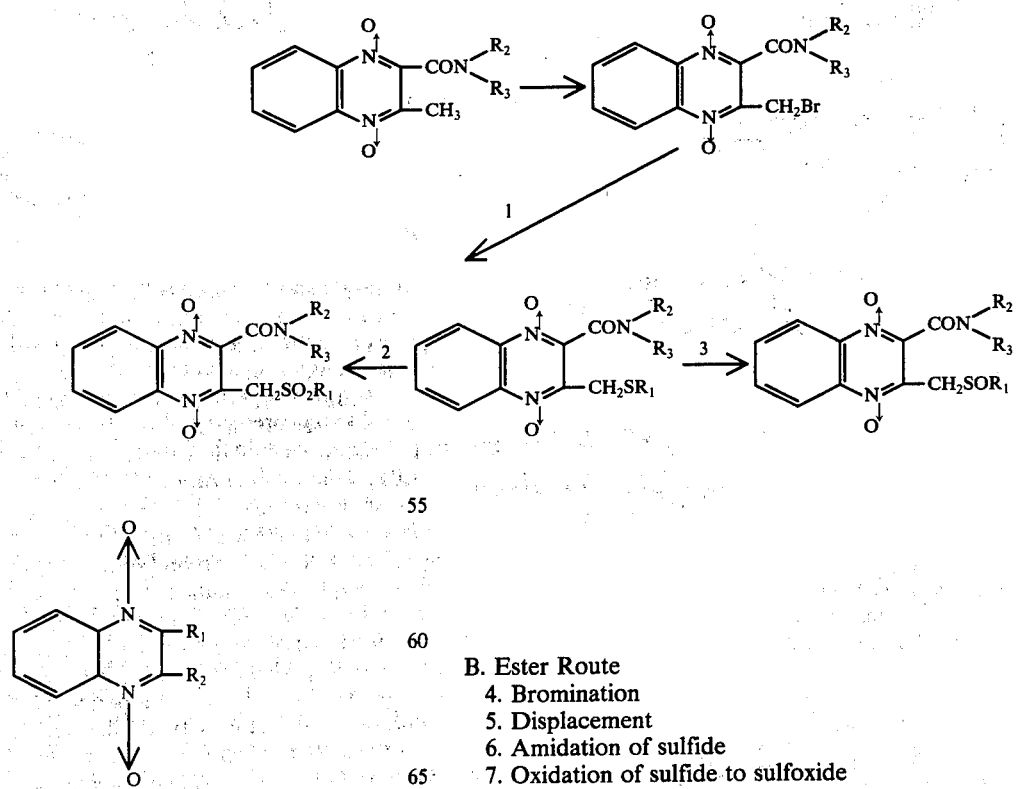

B. Ester Route
 4. Bromination
 5. Displacement
 6. Amidation of sulfide
 7. Oxidation of sulfide to sulfoxide
 8. Oxidation of sulfide to sulfone
 9. Amidation of sulfoxide
 10. Amidation of sulfone

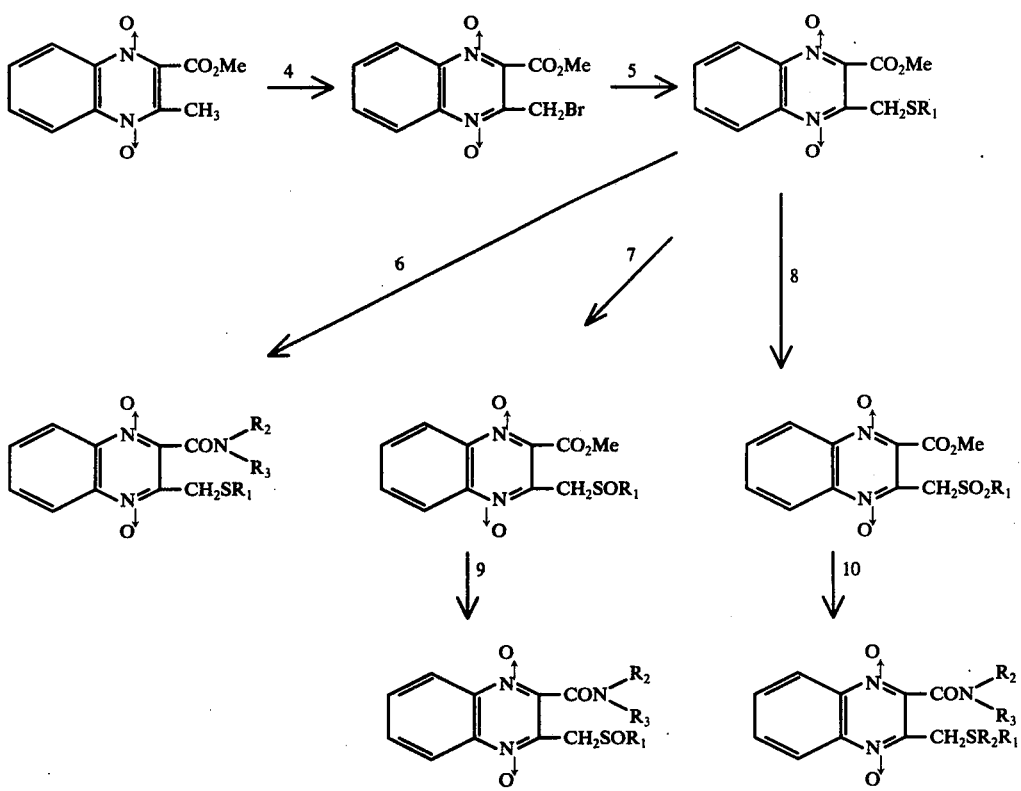

C. Alcohol Route
11. Bromination
12. Displacement

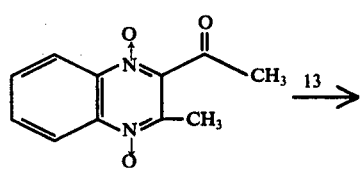

D. Ketone Route
13. Bromination
14. Displacement

-continued

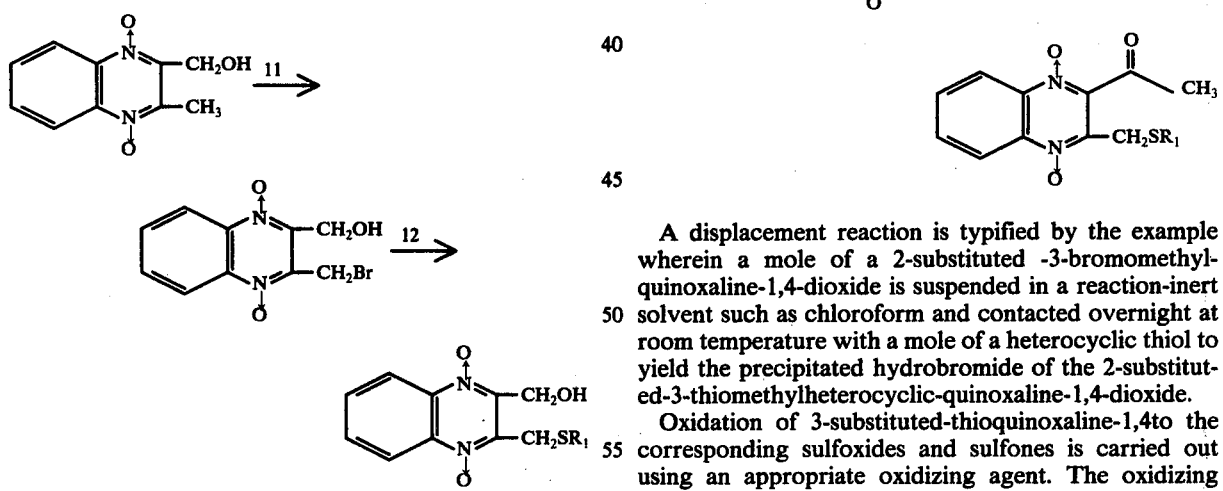

A displacement reaction is typified by the example wherein a mole of a 2-substituted -3-bromomethyl-quinoxaline-1,4-dioxide is suspended in a reaction-inert solvent such as chloroform and contacted overnight at room temperature with a mole of a heterocyclic thiol to yield the precipitated hydrobromide of the 2-substituted-3-thiomethylheterocyclic-quinoxaline-1,4-dioxide.

Oxidation of 3-substituted-thioquinoxaline-1,4to the corresponding sulfoxides and sulfones is carried out using an appropriate oxidizing agent. The oxidizing agent of choice is m-chloroperbenzoic acid. A solution of the appropriate sulfide in a reaction-inert solvent, e.g., chloroform or methylene chloride, is treated, in the case of sulfoxide formation, with an equimolar amount of m-chloroperbenzoic acid. The reaction is usually carried out at 0°–50° C. for a period of 3–24 hours depending on the reactivity of the sulfide reactant. A convenient workup procedure consists of washing the reaction mixture with sodium bicarbonate solution followed by drying and removal of the reaction solvent.

The aforesaid procedure is also employed for the preparation of the corresponding sulfones except that 2 moles of said oxidizing agent is used for each mole of sulfide reactant. The sulfone may also be obtained by oxidation of the sulfide in aqueous acid solution at about 5° C. with aqueous permanganate solution followed by careful permanganate decolorization with a small amount of 30% hydrogen peroxide.

Bromination of a quinoxaline-1,4-dioxide is accomplished by the dropwise addition of excess bromine to a solution or suspension of the compound in methanol or dimethylformamide. The reaction medium is stirred at room temperature until there is no further decolorization of bromine. The product is obtained by precipitation with ether or removal of the reaction solvent.

A 3-substituted carboxylic methyl ester of a quinoxaline-1,4-dioxide may be converted to the corresponding carboxamide by adding the compound to 40% methylamine solution. The precipitate that forms after about ½ hour at room temperature is collected by filtration and washed with water. Substituted carboxamides may be similarly prepared using appropriate amines in place of methylamine.

The compounds of this invention exhibit activity against a wide variety of microorganisms including gram-positive and gram-negative bacteria. In vitro tests are conducted in nutrient media by the usual two-fold serial dilution technique. Results are expressed as the "minimum inhibitory concentration" (M.I.C.) which is the minimum concentration of the compound (in micrograms per milliliter) at which growth of the test microorganism failed to occur.

The in vivo activity of the compounds of this invention can be demonstrated by the protection afforded against experimentally infected animals. For oral administration dosages of from about 1 mg/kg to about 60 mg/kg of body weight are favored. This can be achieved by a number of methods including dosage unit formulations such as capsules, tablets, lozenges, troches, liquid mixtures and solutions. In the case of poultry and domestic animals other methods include mixing the compound with feed or administering the compound as a dilute solution or suspension, e.g., a 0.1% solution for drinking purposes.

The compounds of this invention are preferably administered by the parenteral route, e.g. by subcutaneous or intramuscular injection, at a dosage from about 10 to 100 mg/kg of body weight. Vehicles suitable for parenteral injection may be either aqueous such as water, isotonic saline, isotonic dextrose, Ringer's solution, or non-aqueous such as fatty oils of vegetable origin (corn, peanut, sesame, cotton seed), dimethylsulfoxide and other non-aqueous vehicles which will not interfere with the therapeutic efficiency of the preparation and are non-toxic in the volume of proportion used(glycerol, propylene glycol, sorbitol).

The compounds of this invention have been evaluated in vivo for effectiveness after a single dose, the dose being administered 0.5 hour after inoculating mice with a lethal concentration of a pathogenic microorganism. Surviving mice were held for four days after treatment and the percent survival calculated. In vitro and in vivo data are shown in Table I.

Additional in vitro data and mouse protection studies are exemplified by the results obtained with methyl 3-(N-methyl-2-imidazolyl)thiomethyl-2-quinoxalinecarboxamide-1,4-dioxide as shown in Tables II and III.

Calves with an induced Pasteurella multocida infection were administered one intramuscular injection of methyl 3-(N-methyl-2-imidazolyl)thiomethyl-2-quinoxalinecarboxamide-1,4-dioxide (10 mg/kg). Results are shown in Table IV.

Growing pigs were infected with swine dysentery and subsequently given 3 consecutive daily intramuscular injections of methyl 3-(N-methyl-2-imidazolyl) thiomethyl-2-quinoxalinecarboxamide-1,4(10 mg/kg). Treatment was initiated on the second day of clinical signs. The results are shown in Table V.

Intramuscular injection of methyl 3-(N-methyl-2-imidazolyl)thiomethyl-2-quinoxalinecarboxamide-1,4-dioxide (10 mg/kg) for 3 consecutive days following systemic infection of calves with Salmonella choleaeusuis was effective in its control of the disease as shown in Table VI.

Young pigs infected intratracheally with Pasteurella multocida and subsequently medicated intramuscularly for 3 consecutive days with 3-(N-methyl-2-imidazolyl)thiomethyl-2-quinoxalinecarboxamide-1,4-dioxide (10 mg/kg) responded quickly to medication as shown in Table VII.

Young chicks systematically infected with Escherichia coli were given 3 consecutive daily injections of 3(N-methyl-22-quinoxalinecarboxamide-1,4-dioxide (20 mg/kg) beginning at disease onset. Results of the studies are shown in Table VIII.

Table I

| $R_1$ | $R_2$ | M.I.C. (mcg/ml) S. pyogenes | M.I.C. (mcg/ml) E. coli | Percent Protection (subcutaneous) E. coli (25 mg/kg) | Percent Protection (subcutaneous) S. pyogenes (50 mg/kg) |
|---|---|---|---|---|---|
| COOCH$_3$ | CH$_2$SO$_2$CH$_2$—(pyridyl) | <0.39 | 12.5 | 10 | 60 |
| CONHCH$_3$ | " | <0.39 | 12.5 | 10 | 60 |
| CONH$_2$ | " | <0.39 | 6.25 | 20 | 0 |
| CONHCH$_2$CHOHCH$_3$ | " | <0.39 | 100 | 20 | 60 |
| CONH(CH$_2$)$_2$N(CH$_3$)$_2$ | " | <0.39 | 50 | 20 | 20 |

Table I-continued

Structure: quinoxaline 1,4-dioxide with $R_1$ at position 2 and $R_2$ at position 3.

| $R_1$ | $R_2$ | M.I.C. (mcg/ml) S. pyogenes | M.I.C. (mcg/ml) E. coli | Percent Protection (subcutaneous) E. coli (25 mg/kg) | Percent Protection (subcutaneous) S. pyogenes (50 mg/kg) |
|---|---|---|---|---|---|
| CON(CH$_3$)$_2$ | | 3.12 | 12.5 | 20 | 90 |
| CONHCH$_2$CH$_2$OCH$_3$ | " | 3.12 | 25 | 20 | 40 |
| CONHCH$_2$CH$_3$ | " | 0.39 | 25 | 30 | 30 |
| COOCH$_3$ | CH$_2$SO$_2$(CH$_2$)$_3$-(pyridine) | 6.25 | 25 | 10 | — |
| CONHCH$_3$ | " | 6.25 | 25 | 0 | — |
| CH$_2$OH | CH$_2$S-(1-methyl-imidazole)·HBr | 50 | 100 | — | 70 |
| COCH$_3$ | " | 25 | 1.56 | — | 10 |
| H | " | — | — | — | 30 |
| COOCH$_3$ | CH$_2$SO$_2$-(pyridine)·HCl | <0.39 | 12.5 | 10 | 60 |
| CONHCH$_3$ | " | 0.78 | 12.5 | 0 | 0 |
| CONHCH$_2$CH$_2$OH | " | <0.39 | 25 | 10 | 0 |
| CONHCH$_2$CH$_3$ | " | <0.39 | 25 | 0 | 0 |
| CONH$_2$ | " | <0.39 | 3.12 | 60 | 50 |
| CON(CH$_3$)$_2$ | " | 1.56 | 12.5 | 0 | 80 |
| CONHCH$_2$OHCH$_3$ | " | 6.25 | 50 | 40 | 70 |
| CONH(CH$_2$)N(CH$_3$)$_2$ | " | 12.5 | 50 | 0 | 10 |
| CONHCH$_2$CH$_3$ | " | 3.12 | 50 | 10 | 30 |
| CONH(CH$_2$)$_3$N(C$_2$H$_5$)$_2$ | " | 3.12 | 50 | 0 | 100 |
| CONHCH$_2$CH$_2$OCH$_3$ | " | 1.56 | 100 | 20 | 20 |
| CONH-n-C$_4$H$_9$ | " | 50 | 100 | 0 | 0 |
| CONH(CH$_3$)$_2$N-(pyridine) | " | 25 | <0.39 | 0 | 100 |
| CONH(CH$_2$)$_3$N(CH$_3$)$_2$ | " | 0.78 | 12.5 | 10 | 60 |
| COOCH$_3$ | CH$_2$S-(pyridine) | <0.39 | 50 | 30 | 0 |
| CONHCH$_3$ | CH$_2$S-(pyridine)·HCl ·HCl | 100 | 200 | 0 | 0 |
| CONHCH$_2$CH$_2$OH | " | <0.39 | 50 | 0 | 0 |
| COOCH$_3$ | CH$_2$SO$_2$-(pyridine) | 3.12 | 3.12 | 0 | 30 |
| CONHCH$_3$ | " | <0.39 | 6.25 | 0 | 50 |
| CONHCH$_2$CH$_3$ | " | 1.56 | 12.5 | 0 | 0 |
| CON(CH$_3$)$_2$ | " | 1.56 | 6.25 | 10 | 10 |
| CONHCH$_2$CH$_2$CH$_3$ | " | 12.5 | 25 | 0 | 0 |
| CONHCH$_2$CH$_2$OCH$_3$ | " | 12.5 | 25 | 0 | 70 |

Table I-continued

| R₁ | R₂ | M.I.C. (mcg/ml) S. pyogenes | M.I.C. (mcg/ml) E. coli | Percent Protection (subcutaneous) E. coli (25 mg/kg) | Percent Protection (subcutaneous) S. pyogenes (50 mg/kg) |
|---|---|---|---|---|---|
| CONH(CH₂)₂N(CH₃)₂ | " | 12.5 | 50 | 0 | 90 |
| CONH(CH₂)₃CH₃ | " | 12.5 | — | 10 | 0 |
| CONH(CH₂)₂N⟨piperidine⟩ |  | 1.56 | 50 | 10 | 100 |
| CONH(CH₂)₂N⟨pyrrolidine⟩ | CH₂SO₂-⟨pyridine⟩·HCl | 1.56 | 12.5 | 10 | 60 |
| CONHCH₂CH₂NC₂H₅ | " | 50 | 50 | 0 | 40 |
| CONH(CH₂)₃N(CH₃)₂ | " | 50 | 200 | 0 | 100 |
| CONHCH₂CH₂NH₂ | CH₂SO₂-⟨pyridine⟩ | 100 | >200 | 0 | 0 |
| CONH(CH₂)₂NHSO₂-⟨quinoline N-oxide⟩ | " | <0.39 | >200 | 20 | 0 |
| CONH(CH₂)₂NHSO₂-⟨HOOC-phenyl-SCH₃⟩ | " | 12.5 | >200 | 40 | 10 |
| COOCH₃ | CH₂S-⟨pyridine⟩-COOH | 200 | >200 | 30 | 20 |
| COOCH₃ | CH₂SO₂-⟨pyridine⟩-COOH | 200 | >200 | 50 | 10 |
| CONH₂ | " | >200 | >200 | 10 | 20 |
| CONHCH₃ | " | >200 | >200 | 30 | 0 |
| CONHCH₂CH₂OH | " | >200 | >200 | 30 | 20 |
| CON(CH₃)₂ | CH₂SO₂-⟨pyridine⟩ | 200 | >200 | 50 | 20 |
| CONHCH₂CH₃ | " | >200 | >200 | 0 | 0 |
| COCH₃ | CH₂SO₂-⟨N-methylimidazole⟩ | <0.39 | 6.25 | — | 20 |
| CH₂OH | " | 6.25 | 12.5 | — | 20 |
| CONHCH₃ | " | 3.12 | 6.25 | — | 60 |
| CONHCH₃ | CH₂S-⟨benzimidazole⟩·HBr | 6.25 | 25 | — | 50 |

Table I-continued
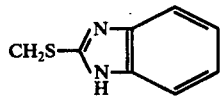
| R₁ | R₂ | M.I.C. (mcg/ml) S. pyogenes | M.I.C. (mcg/ml) E. coli | Percent Protection (subcutaneous) E. coli (25 mg/kg) | Percent Protection (subcutaneous) S. pyogenes (50 mg/kg) |
|---|---|---|---|---|---|
| COCH₃ | " | 6.25 | 200 | — | 0 |
| CH₂OH | 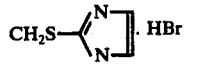 | >200 | >200 | — | 20 |
| COCH₃ | 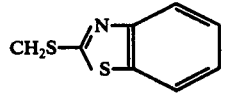 · HBr | 0.78 | 3.12 | — | 30 |
| CONHCH₃ | " | 6.25 | 12.5 | — | 70 |
| CH₂OH | " | 50 | 50 | — | 30 |
| H | " | — | — | — | 30 |
| CONHCH₃ | 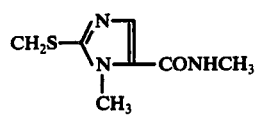 | 200 | >200 | — | 50 |
| COCH₃ | " | — | — | — | 30 |
| COCH₃ | 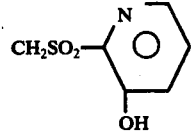 | 25 | 50 | — | 10 |
| COOCH₃ | 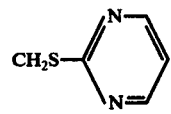 | 3.12 | 25 | 10 | 40 |
| CONH₂ | " | 6.25 | 50 | 10 | 0 |
| COOCH₃ | 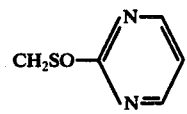 | <0.39 | 25 | 0 | 0 |
| CONHCH₃ | " | <0.39 | 12.5 | 20 | 0 |
| COOCH₃ | 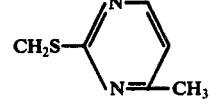 | 3.12 | 25 | 0 | 10 |
| COOCH₃ | 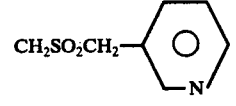 | 50 | 100 | 20 | 10 |
| CONH₂ | " | 12.5 | 12.5 | 0 | 0 |
| CONHCH₃ | " | — | 200 | 0 | 0 |
| COOCH₃ |  | 1.56 | 12.5 | 20 | 60 |
| CONHCH₃ | " | 1.56 | 25 | 30 | 60 |
| CONHCH₂CHOHCH₃ | " | >0.39 | 50 | 30 | 20 |
| CONH₂ | " | 1.56 | 3.12 | 50 | 70 |

Table II

| | Methyl 3-(N-methyl-2-imidazolyl)thiomethyl-2-quinoxalinecarboxamide-1,4-dioxide |
|---|---|
| Organism | M.I.C. (μg/ml) |
| Staphylococcus aureus 01A005 | 3.12 |
| Staphylococcus aureus 01A106 | 3.12 |
| Escherichia coli 51A266 | 12.5 |
| Escherichia coli 51A203 | 12.5 |
| Escherichia coli 51A218 | 6.25 |
| Streptococcus equi 021001 | 0.78 |
| Streptococcus pyogenes 020203 | 3.12 |
| Streptoccoccus zooepidemicus 02H001 | 6.25 |
| Salmonella typhimurium 58D001 | 25 |
| Salmonella dublin 58U001 | 25 |
| Salmonella choleraesuis 58B242 | 12.5 |
| Pasteurella multocida 59A004 | 6.25 |
| Pasteurella multocida 59A002 | 6.25 |
| Pasteurella multocida 59A006 | 6.25 |
| Clostridium perfringens | < 0.39 |

Table III

| Infecting Organism | $PD_{50}$ (mg/kg) Mice | |
|---|---|---|
| | Oral | Subcutaneous |
| Salmonella choleraesuis 58B242 | 9.9 | 11.2 |
| Pasteurella multocida 59A006 | 14.0 | 15.5 |

Table IV

| | Bovine Pasteurellosis | | |
|---|---|---|---|
| Treatment | ADF* Index | ADG** Index | Mortality % |
| Infected Control | — | <0 | 60 |
| methyl 3-(N-methyl-2-imidazolyl)thiomethyl-2-quinoxalinecarboxamide-1,4-dioxide (10 mg/kg) | 90 | 76 | 20 |

*Average daily feed as percent of non-infected control
**Average daily gain as percent of non-infected control

Table V

| | Swine Dysentery | | |
|---|---|---|---|
| Treatment | ADF Index | ADG Index | Mortality % |
| Infected Control | 58 | <0 | 0 |
| methyl 3-(N-methyl-2-imidazolyl)thiomethyl-2-quinoxalinecarboxamide-1,4-dioxide (10 mg/kg × 3) | 101 | 111 | 0 |

Table VI

| | Bovine Salmonellosis | | |
|---|---|---|---|
| Treatment | ADF Index | ADG Index | Mortality % |
| Infected Control | 50 | <0 | 50 |
| methyl 3-(N-methyl-2-imidazolyl)thiomethyl-2-quinoxalinecarboxamide-1,4-dioxide (10 mg/kg × 3) | 95 | 83 | 10 |

Table VII

| | Swine Pasteurellosis | | |
|---|---|---|---|
| Treatment | ADF Index | ADG Index | Mortality % |
| Infected Control | 67 | 50 | 33 |
| methyl 3-(N-methyl-2-imidazolyl)thiomethyl-2-quinoxalinecarboxamide-1,4-dioxide (10 mg/kg × 3) | 105 | 102 | 0 |

EXAMPLE I

Methyl 3-bromomethyl-2-quinoxalinecarboxylate-1,4-dioxide

Methyl 3-methyl-2-quinoxalinecarboxylate-1,4-dioxide (1.2 moles) were suspended in 475 ml of dimethylformamide and 64 ml of bromine was added dropwise with stirring over 1.5 hours while the temperature rose to 42° C. After additional stirring for 48 hours 1.5 liters of methanol were added and stirred for about ½ hour. The precipitated product was removed by filtration, washed with water and dried. Yield, 251 grams (68%); m.p. 113°–16° C.

EXAMPLE 2

Methyl 3-(N-methyl-2-imidazolyl)thiomethyl-2-quinoxalinecarboxylate-1,4-dioxide Methyl 3-bromomethyl-2-quinoxalinecarboxylate-1,4-dioxide (20 mmoles) was dissolved in 100 ml of chloroform and 2-mercapto-1-methylimidazole (22 mmoles) was added in one portion. The precipitate of the hydrobromide which formed after 2 hours stirring at room temperature was collected by filtration, washed with chloroform and dried. Yield, 7.5 grams (88%); m.p. 162–3° C.

EXAMPLE 3

Methyl 3-(N-methyl-2-imidazolyl)thiomethyl-2-quinoxalinecarboxamide-1,4-dioxide Methyl 3-bromomethyl-2-quinoxalinecarboxamide-1,4-dioxide (0.24 moles) was suspended in 1 liter of chloroform with stirring and N-methyl-2-mercaptoimidazole (0.24 moles) was added as a solid. A complete solution resulted within 10 minutes. The solution was stirred overnight at room temperature during which time the desired product crystallized as the hydrobromide. The product was collected by filtration and dried. Yield, 96 grams (91%); m.p. 148–52° C.

EXAMPLE 4

Methyl 3-(N-methyl-2-imidazolyl)sulfonylmethyl-2-quinoxalinecarboxamide-1,4-dioxide A solution of methyl 3-(N-methyl-2-imidazolyl)thiomethyl-2-quinoxalinecarboxamide-1,4-dioxide (2.9 mmoles) in 30 ml of chloroform was stirred while m-chloroperbenzoic acid (6.4 mmoles) was added in one portion. The solution, after stirring overnight at room temperature, was filtered to remove m-chlorobenzoic acid. The filtrate was washed with 5% $NaHCO_3$ solution, dried over $K_2CO_3$ and evaporated to a yellow solid. Yield, 0.562 grams (51%); m.p. 176–81° C. (dec.).

EXAMPLE 5

Methyl 3-[(4-pyridyl)-sulfinylmethyl]-2-quinoxalinecarboxylate-1,4-dioxide

Methyl 3-[(4-pyridyl)-thiomethyl]-2-quinoxalinecarboxylate-1,4-dioxide (0.03 moles) in 120 ml of chloroform was treated dropwise with m-chloroperbenzoic acid (0.03 moles) in 80 ml of chloroform at 0°–5° C. The solution after 2 hours was washed with 5% $NaHCO_3$ solution (3 × 200 ml), water (1 × 60 ml) and then dried over sodium sulfate. The chloroform solution was concentrated to a small volume and added with stirring to 300 ml of ether to precipitate the desired product. Yield, 10.1 grams (94%); m.p. 137–39° C. (dec.).

EXAMPLE 6

Methyl 3-[(4-pyridyl)-thiomethyl]-2-quinoxalinecarboxamide-1,4-dioxide

Methyl 3-[(4-pyridyl)-thiomethyl]-2-quinoxalinecarboxylate-1,4-dioxide (2.92 mmoles) was added in one portion to 10 ml of 40% methylamine solution to give a blue solution. A precipitate, after ½ hour, was collected by filtration and washed with water. The material was recrystallized from chloroform-ether. Yield, 0.54 grams (54%); m.p. 179–82° C.

EXAMPLE 7

Methyl 3-[(2-pyridyl)-sulfonylmethyl]-2-quinoxalinecarboxylate, 1,4-dioxide

Methyl 3-[(2-pyridyl)-thiomethyl]-2-quinoxalinecarboxylate-1,4-dioxide (0.03 moles) in 60 ml of acetone was cooled to 0°–5° C. and 50 ml of 2N $H_2SO_4$ was added in one portion. This was followed by the dropwise addition of a solution of $KMnO_4$ (0.04 moles) in 150 ml of water over a 20 minute period. The mixture was stirred for about 5 minutes at which time 4 ml of 30% $H_2O_2$ was added very carefully dropwise to decolorize the purple solution. The desired product, which had precipitated, was collected by filtration and washed with water. Yield, 8.12 grams (87%); m.p. 154° C. (dec.).

EXAMPLE 8

Methyl 3-[(4-pyridyl)-sulfonylmethyl]-2-quinoxalinecarboxamide-1,4-dioxide

Methyl 3-[(4-pyridyl)-sulfonylmethyl]-2-quinoxalinecarboxylate-1,4-dioxide (2.7 mmole) was added to 10 ml of 40% methylamine solution to give a dark red mixture which was allowed to stand at room temperature for about 1 hour. The precipitate was collected by filtration and washed with ether. Yield, 0.85 grams (85%); m.p. 220° C. (dec.).

EXAMPLE 9

2-bromomethyl-3-hydroxymethylquinoxaline-1,4-dioxide

2-Hydroxymethyl-3-methylquinoxaline-1,4-dioxide (1 mole) was suspended in 5 liters of methanol and stirred while bromine (1.06 moles) was added dropwise over 1.5 hours. The reaction mixture was stirred for 5 days. The product was collected by filtration and washed with 1 liter of ether/400 ml methanol and then with 1 liter of ether. Yield, 175 grams (61%); m.p. 149°–150° C.

EXAMPLE 10

3-(N-methyl-2-imidazolyl)thiomethyl-2-hydroxymethylquinoxaline-1,4-dioxide

2-Bromomethyl-3-hydroxymethylquinoxaline-1,4-dioxide (0.01 mole) was suspended in 75 ml of chloroform and 2-mercapto-1-methylimidazole (0.01 mole) was added in one portion. The suspension was stirred at room temperature for about 2 hours. The product was collected by filtration. Yield, 3.82 grams (96%); m.p. 174–7°).

EXAMPLE 11

2-acetyl-3-bromomethylquinoxaline-1,4-dioxide

To a stirred suspension of 2-acetyl-3-methylquinoxaline-1,4-dioxide (1.57 moles) in 3 liters of methanol and added bromine (1.74 moles) over a period of 2 hours. The reaction mixture was then stirred for 5 days at room temperature. The resulting yellow solid was collected by filtration, washed with methanol and ether. Yield, 331 grams (71%); m.p. 164–6° C.

EXAMPLE 12

3-(N-methyl-2-imidazolyl)thiomethyl-2-acetylquinoxaline-1,4-dioxide

2-Acetyl-3-bromomethylquinoxaline (0.01 mole) was dissolved in 75 ml of chloroform and 2-mercapto-1-methylimidazole was added in one portion. The solution was stirred at room temperature for about 1.5 hours. The hydrobromide was collected by filtration and washed with chloroform. Yield, 3.99 grams (97%); m.p. 196° C.

EXAMPLE 13

The methods of Examples 1 to 12 were repeated with the desired heterocycle introduced by the method of Example 2 and the desired amido group employing the appropriate amine by the method of Example 6 to produce the following compounds:

| $R_1$ | $R_2$ | m.p. (° C.) |
|---|---|---|
| CONHCH$_2$CH$_2$OH | 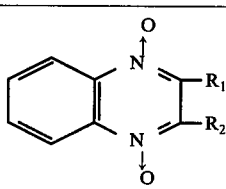 | 179–81 (free base) |
| CONH$_2$ | " | 202–6 |
| CONHCH$_2$CH$_2$N(CH$_3$)$_2$ | " | 159–62 (free base) |
| CON(CH$_3$)$_2$ | " | 214–15 |

-continued

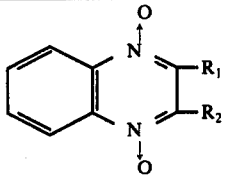

| R₁ | R₂ | m.p. (° C.) |
|---|---|---|
| CONHCH₃ | 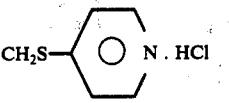 | 127–33 |
| CONHCH₂CH₂OH | " | 182–4 |
| CONHCH₂CH₃ | " | 171–3 |
| CONH₂ | " | 225–8 |
| CON(CH₃)₂ | " | 192–3 |
| CONHCH₂CHOHCH₃ | " | 179 |
| CONHCH₃ | 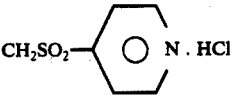 | 163 |
| CONHCH₂CH₂OH | " | 158–9 |
| CONHCH₂CH₃ | " | 214–5 |
| CONHCH₂CH₃ | 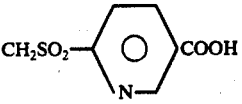 | 237–40 |
| COOCH₃ | | 149–54 |
| COOCH₃ | 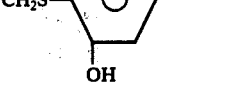 | 171–5 |
| CONH₂ | " | 245–6 |
| COOCH₃ |  | 153–65 |
| CONHCH₃ | " | 207–8 |
| COOCH₃ | 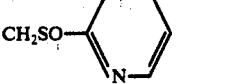 | 140–3 |
| COOCH₃ | 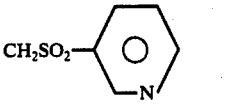 | 136–40 |
| CONH₂ | " | 211–12 |
| CONHCH₃ | " | 204–5.5 |
| COOCH₃ | | 146–50 |
| CONHCH₃ | 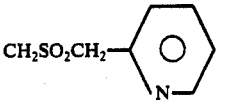 | 185–8 |
| CONHCH₂CHOHCH₃ | " . HCl | 189–93 (free base) |
| CONH₂ | " | 203 |
| COOCH₃ | " | 129–34 |
| | CH₂SO₂CH₂- pyridyl | |
| CONHCH₃ | " | 199–201.5 |
| CONH₂ | " . HCl | 215–16 |
| CONHCH₂CHOHCH₃ | " | 196–8 |
| CONH(CH₂)₂N(CH₃)₂ | " . HCl | 123–6 |
| CON(CH₃)₂ | " . HCl | — |
| CONHCH₂CH₂OCH₃ | " | 176–9 |

-continued

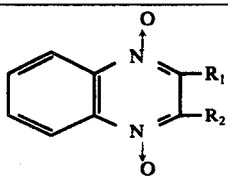

| R₁ | R₂ | m.p. (° C.) |
|---|---|---|
| CONHCH₂CH₃ | " | 208-9 |
| COOCH₃ | CH₂SO₂(CH₂)₃-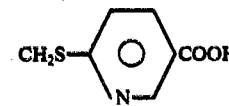 | 129-34 |
| CONHCH₃ | " | 169-71 |
| H | CH₂S-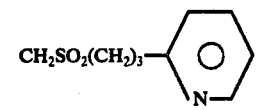.HBr | 204-5 |
| COCH₃ | CH₂SO₂-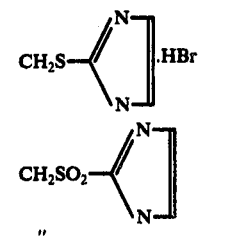 | 169-72 |
| CONHCH₃ | " | 198-9 |
| CH₂OH | " | 198-9 |
| CONHCH₃ | CH₂S₂-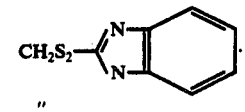.HBr | 196-9 |
| CH₂OH | " | 198-200 |
| COCH₃ | " | 215-17 |
| COCH₃ | CH₂S-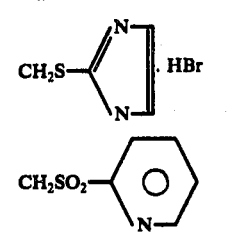.HBr | 211-12 |
| CONHCH₂CH₂CH₃ | CH₂SO₂- | 204-5 |
| CONHCH₂CH₂OCH₃ | " | 172-6 |
| CONHCH₂CH₂N(CH₃)₂ | " | 172-4 |
| CONH(CH₂)₃CH₃ | " | 197-8 |
| CONH(CH₂)₂N⟨piperidine⟩ | ". HCl | 200-3 |
| CONH(CH₂)₂N⟨pyrrolidine⟩ | " " | 178-85 |
| CONHCH₂CH₂N(CH₂CH₃)₂ | " " | 164-66 (free base) |
| CONH(CH₂)₃N(CH₃)₂ | " " | 202-3 |
| CONHCH₂CH₂NH₂ | " " | 156-7 |
| CONH(CH₂)₂NHSO₂- | " " | 147-8 |
| CONH(CH₂)₂NHSO₂-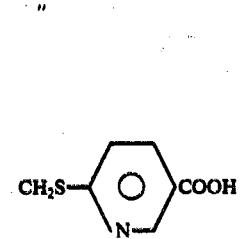 | " | 145-52 |
| COOCH₃ | CH₂S-[pyridine with COOH] | 125-30 |

-continued

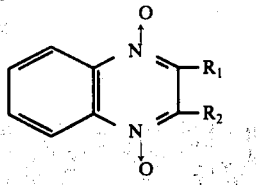

| R₁ | R₂ | m.p. (° C.) |
|---|---|---|
| COOCH₃ | 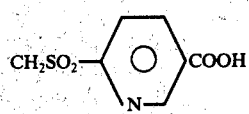 | 184-7 |
| CONH₂ | " | 205-9 |
| CONHCH₃ | " | 225-30 |
| CONHCH₂CH₂OH | " | 225-6 |
| CON(CH₃)₂ | " | 188-90 |
| CONH₂ | 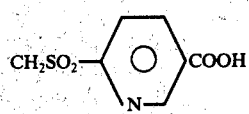 | 168-71 |
| CON(CH₃)₂ | " | 205-6 |
| CONHCH₂CHOHCH₃ | " . HCl | 159-60 |
| CONHCH₂CH₂N(CH₃)₂ | " " | 183-4 |
| CONHCH₂CH₂CH₃ | " | 173-4 |
| CONHCH₂CH₂OCH₃ | " | 191-3 |
| CONHCH₂CH₂N(CH₂CH₃)₂ | " . HCl | 165-8 (free base) |
| CONH-n-C₄H₉ | " | 176 |
| CONHCH₂CH₂N⟨piperidine⟩ | " | 162-4 |
| CONH(CH₂)₃N(CH₃)₂ | " | 144-5 |
| COOCH₃ | 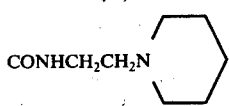 | 152 |
| CONHCH₃ | " | 222 |
| CONHCH₂CH₂OH | " | 168-70 (free base) |
| COOCH₃ | 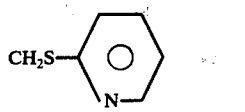 | 154 |
| CONHCH₃ | " | 208.5-10 |
| CONHCH₂CH₃ | " | 202-3 |
| CON(CH₃)₂ | " | 195-7 |
| CONHCH₃ | 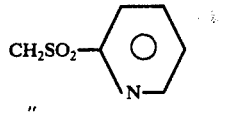 | 181-6 |
| CH₂OH | " " | 183-4 |
| H | " " | 198-200 |
| CONHCH₃ | 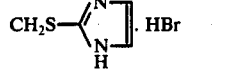 | 169-73 |
| COCH₃ | " | 150-4 |
| COCH₃ | 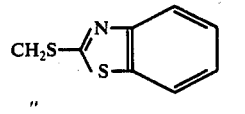 | 185-6 |
| H | 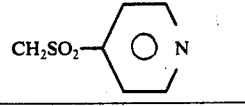 | 206-9.5 |

What is claimed is:
1. A compound having the formula

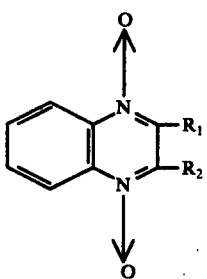

and the pharmaceutically-acceptable acid addition salts thereof, wherein $R_1$ is hydrogen, acetyl, hydroxymethyl, or

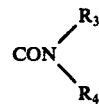

where $R_3$ and $R_4$ are hydrogen, lower alkyl, lower hydroxyalkyl or lower aminoalkyl; and $R_2$ is $CH_2S(O)_m$—$(CH_2)_n$- heterocycle where $m$ is 0 or 2, $n$ is 0, 1 or 3 and the heterocycle is selected from the group consisting of 2-imidazolyl, N-methyl-2-imidazolyl, pyridyl, 2-benzimidazolyl, 2-pyrimidinyl and 2-benzthiazolyl.

2. A method of controlling pasteurellosis and salmonellosis in animals which comprises administering to said animals a compound of claim 1 at a level of at least 10 mg/kg/day.

3. Methyl 3-(N-methyl-2-imidazolyl)thiomethyl-2-quinoxalinecarboxamide1,4-dioxide.

4. The method of claim 2 wherein said compound is methyl 3-(N-methyl-2-imidazolyl)thiomethyl-2-quinoxaline-carboxamide-1,4-dioxide.

* * * * *